(12) United States Patent
Choudhary et al.

(10) Patent No.: US 8,889,733 B2
(45) Date of Patent: Nov. 18, 2014

(54) **ARTONIN I TO TREAT RESISTANT INFECTIOUS *STAPHYLOCOCCUS AUREUS***

(71) Applicants: Muhammad Iqbal Choudhary, Karachi (PK); Saba Farooq, Karachi (PK); Atia-tul Wahab, Karachi (PK); Christian D. A. Fozing, Yaounde (CM); Atta-ur Rahman, Karachi (PK)

(72) Inventors: Muhammad Iqbal Choudhary, Karachi (PK); Saba Farooq, Karachi (PK); Atia-tul Wahab, Karachi (PK); Christian D. A. Fozing, Yaounde (CM); Atta-ur Rahman, Karachi (PK)

( * ) Notice: Subject to any disclaimer, the term of this patent is extended or adjusted under 35 U.S.C. 154(b) by 0 days.

(21) Appl. No.: 13/740,919

(22) Filed: Jan. 14, 2013

(65) Prior Publication Data
US 2014/0200189 A1    Jul. 17, 2014

(51) Int. Cl.
| | | |
|---|---|---|
| *A61K 31/35* | (2006.01) | |
| *A61K 31/70* | (2006.01) | |
| *A61K 31/352* | (2006.01) | |
| *A61K 31/165* | (2006.01) | |
| *A61K 31/42* | (2006.01) | |
| *A61K 31/43* | (2006.01) | |
| *A61K 31/431* | (2006.01) | |
| *A61K 31/496* | (2006.01) | |
| *A61K 31/7036* | (2006.01) | |
| *A61K 31/7048* | (2006.01) | |
| *A61K 31/7056* | (2006.01) | |
| *C07D 311/30* | (2006.01) | |

(52) U.S. Cl.
CPC ............. *A61K 31/352* (2013.01); *A61K 31/165* (2013.01); *A61K 31/42* (2013.01); *A61K 31/43* (2013.01); *A61K 31/431* (2013.01); *A61K 31/496* (2013.01); *A61K 31/7036* (2013.01); *A61K 31/7048* (2013.01); *A61K 31/7056* (2013.01); *C07D 311/30* (2013.01)
USPC ................. 514/456; 514/24; 514/29; 514/37; 514/39; 514/40; 514/196; 514/199; 514/253.08; 514/378

(58) Field of Classification Search
USPC .......................................................... 514/456
See application file for complete search history.

*Primary Examiner* — Elli Peselev
(74) *Attorney, Agent, or Firm* — Sarfaraz K. Niazi

(57) ABSTRACT

Artonin I is reported to treat multi-drug resistant *Staphlococcus* infections.

2 Claims, 4 Drawing Sheets

ARTONIN I TO TREAT RESISTANT INFECTIOUS *STAPHYLOCOCCUS AUREUS*

BACKGROUND OF THE INVENTION

A rapid decline in research and development of new antibiotics coincides with increasing frequency of infections caused by multi-drug-resistant pathogens. The key reason of bacterial resistance is the indiscriminate use of antibiotics (Zunita et al., 2008). The outbreak of methicillin-resistant *Staphylococcus aureus* (MRSA), occurred over fifty years ago (Habte-Gabr et al., 2010), and is now widespread throughout the world. *S. aureus* is the most common bacterial pathogen, which causes skin, soft-tissue, and endovascular infections, pneumonia, septic arthritis, endocarditis, osteomyelitis, and sepsis (David et al., 2010). MRSA has now mutated for decades with increasing incidence of community associated (CA) infections, often producing painful pus filled lesions of deep tissues (Kumar et al., 2010).

In Europe mortality rates due to hospital acquired infections by resistant bacteria has exceeded more than 25,000 annually (World Health Organization 2012). In 2005, a report submitted by the Centers for Disease Control and Prevention (CDC, USA) indicated that more than 94,000 people developed life-threatening infections caused by MRSA, and about 19,000 people died due to nocosomial MRSA infections.

At present, MDR diseases are among the most common causes of premature mortality all over the world. Therefore, there is a strong need in resource limited countries, like Pakistan, to review the utility of conventional antibiotics for the management of skin and soft tissue infections, caused by MRSA (Idrees et al., 2009) and to resume research globally in the field of multi-drug resistant infections with innovative approaches.

According to research, 35% MRSA is present in Pakistan. The Central Laboratory could only isolate 792 (91%) live *Staphylococcus aureus* out of a total of 875 isolates received, from which 332 (42%) were identified as MRSA. The prevalence of MRSA among cities differs with the highest being from Lahore (61%), (57.5%) in Karachi, Rawalpindi/Islamabad having (46%) and (36%) in Peshawar while Sukkur had only 2% MRSA (Sattar et al., 2011; Butt, et al., 2004).

Reported MDR inhibitor 5'-methoxyhydnocarpin (5'-MHC) was isolated from berberine which is produced by *Berberis* plants (Lewis et al., 2001). Reserpine, an alkaloid from *Rauwolfia vomitoria* root bark is a well-known bacterial efflux inhibitor against mammalian and for gram-positive organism as well. Reserpine, has activity against one of the *Staphylococcus aureus* pump's NorA, which contributes to fluoroquinolone resistance in clinical isolates (Mullin et al., 2004). The most common mechanism of resistance in bacteria includes the efflux pumps capable of excreting out a wide range of antibiotics and xenobiotics (Nelson et al., 2002).

The five major mechanisms of antimicrobial resistance include, (i) alterations in the site of action (Coates et al., 2002) (ii) the steps targeted for inhibition can be by-passed. (iii) the intracellular concentration of the drug is reduced (Coates et al., 2002), (iv) inactivation of the antibiotics, and (v) the overproduction of target enzymes (Wright et al., 2005). These mechanisms are mediated by mutation resulted both by horizontal and vertical gene transfer.

There are three main approaches to meet the challenge associated with growing antibiotics resistance:
a. Discovery of new antibiotics, both from natural and synthetic sources.
b. Modifications in the structures of existing antibiotics to synthesize new analogues with enhanced antibiotic properties, and
c. Discovery of "helper" molecules, which help the existing antibiotics to act more effectively by reversing the resistance mechanisms.

Among them, the third approach has special significance as it addresses the microbial resistance as the core, i.e., molecular level, and increases the life span of existing antibiotics. These helper molecules possibly can block the efflux pumps, depolarizes the membrane potential, revert the resistance by increasing the susceptibility of already ineffective drugs, and induced ROS production in resistant microorganisms. During the current study we discovered aflavonoid, isolated from genus *Morus inesozygia* Stapf., as highly active and reproducible inhibitors against all tested strains of *S. aureus*. *Morus inesozygia* (Moraceae) is a shrub from the tropical and subtropical regions of the world. Stems and the leaves of the plant are used to treat different diseases such as syphilis, dermatitis, rheumatism, asthenias, fever and malaria (Berhaut, 1979, Burkill, 1997). Methanolic extract and isolated compounds from *Morus inesozygia* are reported to have antimicrobial (Kuete et al., 2009) and antioxidant activities (Kapche et al., 2009). Some compounds, isolated from the leaves of *Morus mesozygia*, have exhibited inhibitory activity against phosphodiestearse 1 enzyme (Fozing et al., 2011). However, use of any of these compounds has never been reported in treating MDR infections based on their ability to reverse the drug resistance and to provide a surprising. synergism with antibiotics traditionally used to treat infections from *Staph aureus*. The description of the source of the isolated compounds is not relevant to the invention as any source yielding these compounds would be sufficient for the purpose of this invention.

BRIEF SUMMARY OF THE INVENTION

In order to fight life threatening conditions caused by resistant microorganisms, consistent effort has been made to discover new and effective bacterostatic and bactericidal agents. As the efficacy of currently available drugs is declining due to MDR, there is an urgent need to develop new approaches to meet this challenge, which is an enduring threat to human survival and wellbeing. The natural products have served as the foundation of all medicinal systems worldwide. For therapeutic purposes, about 20,000 plant species are used globally, many of which are known to be effective against infectious diseases. In the present study, we discovered that two flavonoids (Compound 1, which is artonin I, the designated name is the IUPAC name) is potent inhibitors of MDR *S. aureus* (EMRSA-17, EMRSA-16, MRSA-252 and clinical isolates) by using high throughput screening methods (Table 1). Resistance-reversal studies were carried out and synergistic and partial synergistic effects of compound 1 along with antibiotics were analyzed. The mechanism of action of compound 1 was investigated by using flow cytometery including membrane alterations and efflux pump inhibitions. Compound-induced ROS production was also studied.

Figure 2:
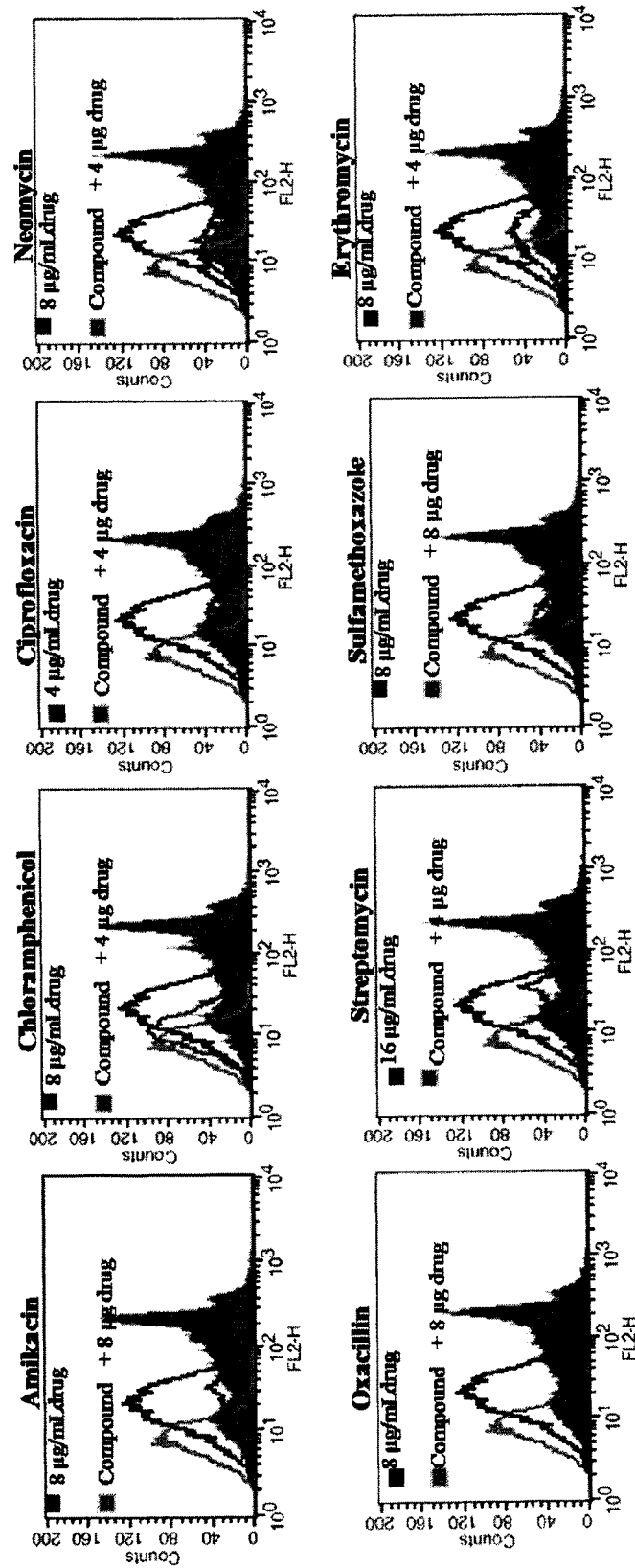

FIG. 2 depicts increased sensitivity of MDR Bacteria EMRSA-17 to drugs by blocking the MDR Efflux Pumps. Flow cytometery histogram showing EtBr accumulation in EMRSA-17. Treated with antibiotic and metal complex alone and in combination (AMK, CHL, CIP, NEO, OXA, STRP, SULF, ERYT).

Figure 3:
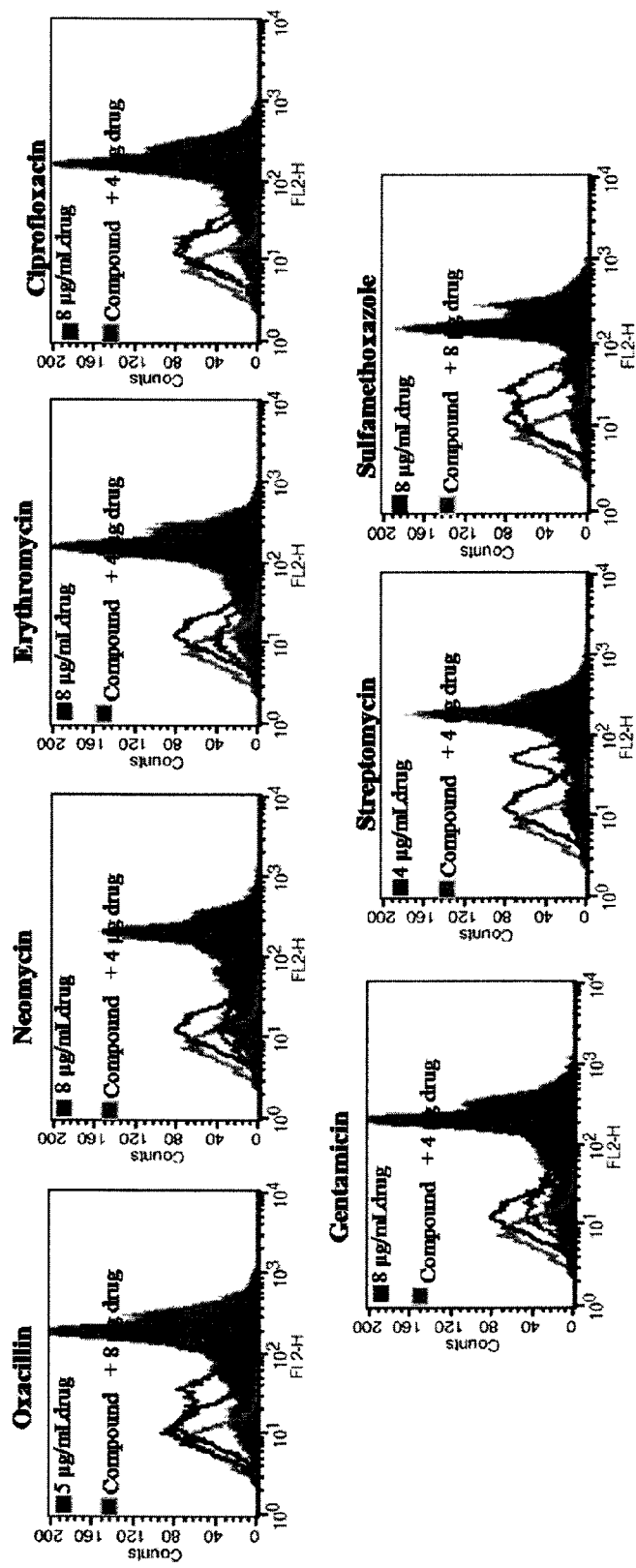

FIG. 3 depicts increased sensitivity of MDR bacteria clinical isolate to drugs by blocking the MDR Efflux Pumps. Flow cytometry histogram, showing EtBr accumulation in clinical isolates. Treated with antibiotic and metal complex alone and in combination (GENT, CIP, NEO, OXA, STRP, SULF, ERYT).

Figure 4:
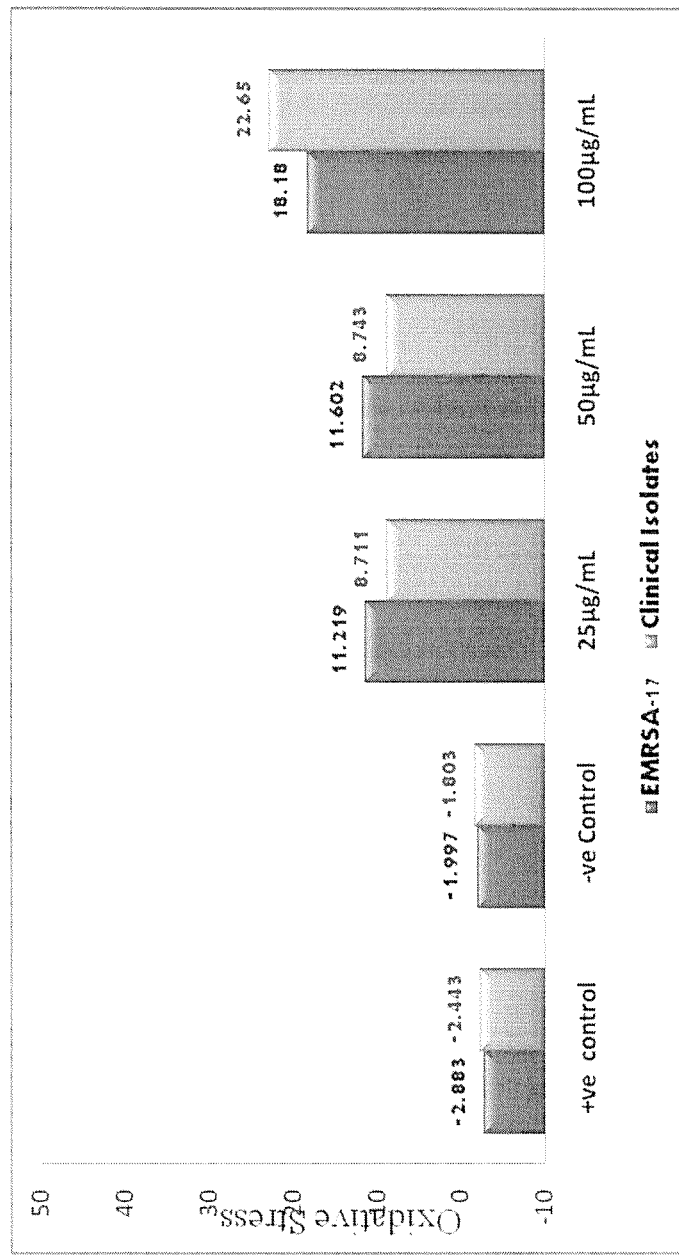

FIG. 4 depicts compound induce damage through generation of Reactive Oxygen Species ($O_2^-$) in cells EMRSA-17 and clinical isolates after the treatment of Compound 1 by using the CL assay with the lucigenin as a detector.

DETAILED DESCRIPTION OF THE INVENTION

The present invention relates to discovery of agents which can have a novel action of reversing, the resistance in infections causing bacteria.

EXAMPLE 1

High throughput screening assay (MABA) against MDR *S. aureus*:

Inocula Preparation: Isolated colonies of *S. aureus* were picked and inoculated into Muller Hinton broth and incubated at 37° C. for 20 hours. After 20 hours, the turbidity was checked and adjusted to 0.5 McFarland standards.

Assay Protocol: Assays were performed according to method reported by Sarkar et al. (2007) with slight modifications. Flat bottom, polystyrene, non-tissue culture treated, sterile 96-well micro titer plates were used with proper labeling. Stock solutions of test compounds 1 and 2 were prepared in DMSO with the concentration of 1 mg/mL. 4 µL from stock solutions were distributed in each well, except the control wells of the plate. Two fold serial dilutions using sterile broth were made with the final volume of 200 g, in each well. The bacterial suspensions (cone $5 \times 10^5$) were then added in each wells. The plate was sealed by parafilm and incubated at 37° C. for 20 hours. The plates were prepared in triplicate. Next day, 10% Alamar Blue Dye was added to the culture and kept on shaking incubator at 37° C. for 3 to 4 hours. The color change was then assessed visually, qualitatively and quantitatively by recording absorbance at 570 and 600 nm by a spectrophotometer. The percentage inhibition of compound 1 and 2 against EMRSA-16, and 17, MRSA-252 and clinical isolate by MABA assays are given in Table 1.

Percentage reduction and inhibition of Alamar blue dye was calculated by using the following formula.

$$\frac{(\varepsilon ox)\lambda 2 A \lambda 1 - (\varepsilon ox)\lambda 1 A \lambda 2}{(\varepsilon red)\lambda 1 A' \lambda 2 - (\varepsilon red)\lambda 2 A'} \times 100$$

Where.

$\varepsilon ox$=molar extinction coefficient of Alamar blue oxidized form (blue)

$\varepsilon red$=molar extinction coefficient of Alamar blue reduced form (pink)

A=absorbance of test wells
A'=absorbance of negative control well
$\lambda 1$=570 nm
$\lambda 2$=600 nm Here control wells contain only media plus Alamar Blue, while the test wells contains both Alamar Blue with the test compounds.

EXAMPLE 2

Effect of Artonin I (1) on the Membrane Potential and Integrity of MDR *S. aureus*:

Compound Treatment: $5 \times 10^5$ MDR *S. aureus* cells were treated with 20 µg/mL of test compounds and incubated for 20 hours, while the control cells were incubated without test compound.

Cell Staining: Staining procedure of Jepras et al. (1997) was adapted with slight modifications. Stock solutions (1 mg/mL) for the membrane potential probe DiBAC4(3) were made in absolute ethanol and stored at −20° C. Cells were allowed to stain at room temperature for 10 min before analysis by flow cytometry. Samples (1 mL) of exponentially growing *S. aureus* were taken from broth cultures. Samples were centrifuged at 11,000 rpm for 2 min and the supernatant was discarded. Cell pellets were resuspended in 4 mL of filtered phosphate-buffered saline (PBS). Fluorogenic substrates DiBAC4(3) were added to the cell suspensions to obtain a final concentration of 10 µg/mL. The suspensions were then incubated at 37° C. for 30 min. Cells were washed by centrifugation in the PBS buffer and then analyzed by flow cytometry.

Flow cytometry data acquisition: The flow cytometric assay was performed on a Becton Dickinson FACSCaliber™ flow cytometer. A total of 50,000 cells were counted by using Cell Quest software (BD) for data acquisition and analysis. The emission maximum of DiBAC4(3) was at 516 nm and its green fluorescence was detected in the channel FL1 (Veal et al., 2000).

Figure 1:
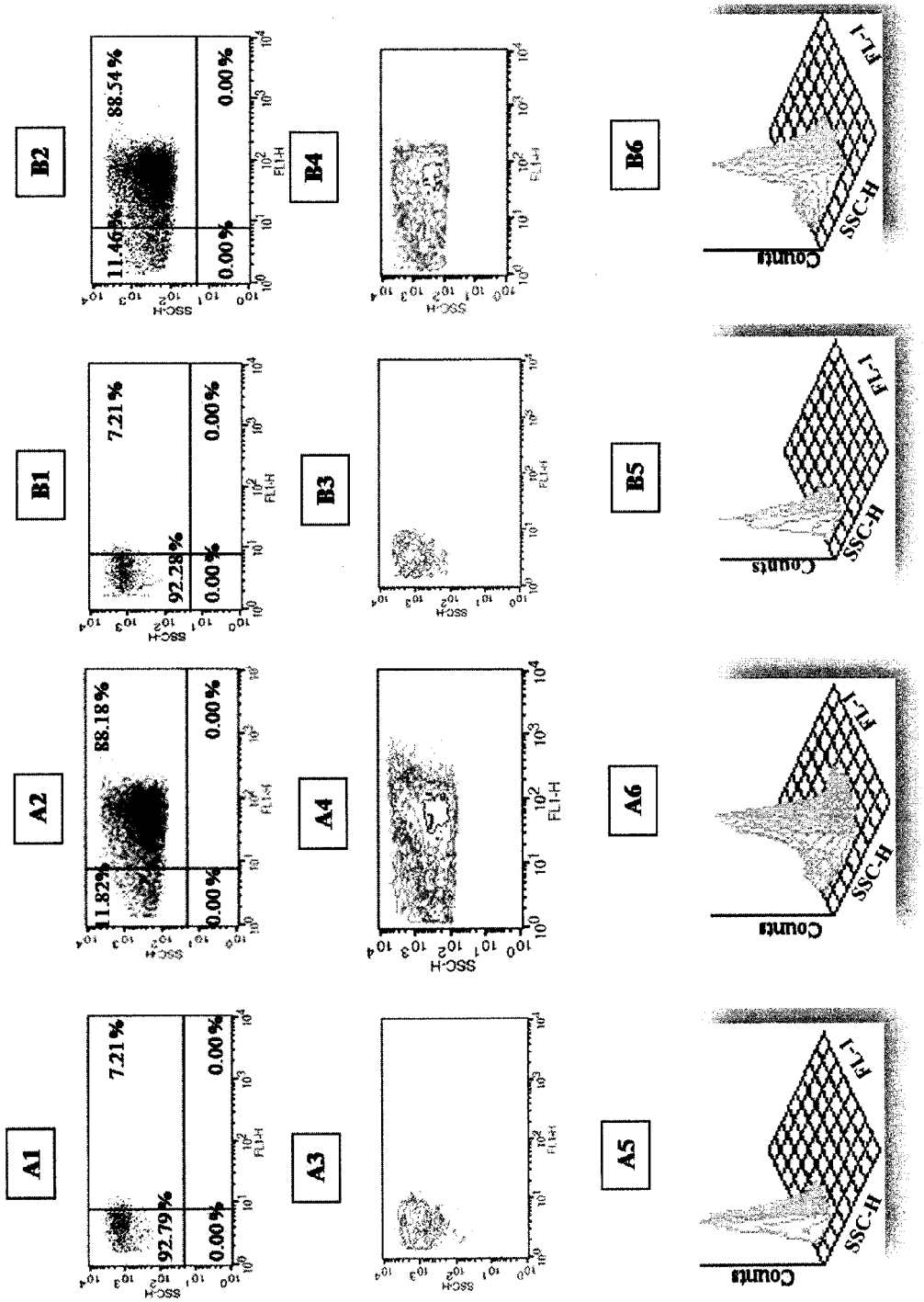
FIG. 1 depicts the effect of artonin I (1) (on the membrane potential and integrity of MDR *S. aureus*. Above Dot plots (A1, A2, B1 and B2), Contour plots (A3, A4, B3 and B4) and 3D plots (A5, A6, B5 and B6) represents the FL1 log DiBAC4 (3) fluorescence versus side scatter (SSC). Light scattering and DiBAC4(3) fluorescence of MDR *S. aureus* (EMRSA-17 and clinical isolates) were taken after 20 hrs of growth without any treatment (A1, A3, A5 and B1, B3 and B5, respectively) and with the treatment of 20 µg/mL conc. of compound 1 (A2, A4, A6, and B2, B4 and B6).

Results: In membrane potential assay, light scattering properties and DiBAC4(3) green fluorescence were measured by Dot, Contour, and 3D plots (FIG. 1). Control dot plots were A1 and B1, while dot plots (A2 and B2) indicates that in treated cells the bulk population is shifted towards FL-1. This indicates a clear discrimination between treated and control cells. Green fluorescence was due to the increased accumulation of dye inside the cell indicating the compound induced membrane changes or damage. Similarly the contours represents the regions of increasing frequency of events (fluorescence) with the large shift in the treated cells (A4 and B4), as compared to the controlled one with the well defined pattern of population.

The same results were shown by 3D plots. The compound induced profound changes in the pattern of peaks. In plot A6 (treated EMRSA-17), the majority of population was shifted in a rapid regular pattern due to the change in membrane potential caused by the presence of natural products 1. In B6 (clinical isolate) cells, bulky peaks steadily moved towards the area of increasing fluorescence mainly due to the binding of dye inside the cellular contents. Treatment with compound 1 resulted in an extensive increase in fluorescence indicative of potential-dependent-distribution between the cytoplasmic membrane and extracellular medium.

Discussion: Flow cytometry is effectively used for the measurement of intrinsic increase of fluorescence DiBAC4 (3). In metabolically active bacteria with intact cytoplasmic membranes, there is typically a difference of electrical potential across the membrane. In bacteria, the generation of membrane potential occurred by the extrusion of protons coupled. This process generates a potential for protons, or proton motive force (PMF).

Our studies on membrane potential indicated that antibiotics had the least effect in cell potential, i.e. neither cause depolarization nor increased or altered permeability even at high concentrations. In contrast, after the treatment of compound 1, the rapid uptake of membrane potential-sensitive dye was observed indicating that the cells were depolarized along with disrupted cytoplasmic membrane.

The fluorescent dye accumulates inside the cells by binding to intracellular proteins and membranes. The loss of membrane potential was measured with the green fluorescent bis-oxonol DiBAC4(3) FL1, 520 nm (Berney, et al., 2006).

EXAMPLE 3

Reversal of Multi-Drug Resistance by Artonin I (1)

Assay Protocol: Protocol of Chung et al, (2001), with slight modifications, was followed. 5×10 MDR S. aureus cells were treated with 20 µg/mL of test compounds and incubated for 20 hours. Control cells were not exposed to any test compound and antibiotic. In 96-well plate, increasing concentration of antibiotics, along with the fixed concentration of test compounds were added. Inoculum of $5 \times 10^5$ cells was applied to all wells. The presence or absence of growth in all combination wells were noted visually and by using the dye Alamar blue.

Fractional inhibitory concentrations were calculated by the above cited formulae.

FIC of Antibiotic a ($FIC_a$)=MIC of Antibiotic a in combination/MIC of antibiotic a alone FIC of Compound b ($FIC_b$)=MIC of Compound b in combination/MIC of compound b alone The sum of Fractional Inhibitory Concentration ($FIC_s$) index of: $(FIC_a)+(FIC_b)=(FIC_s)$ Results: The results of reversal resistance studies of compound 1 with different classes of antibiotics against MDR S. aureus, EMRSA-17 and clinical isolates are present in Table 2 and 3. The MIC of compound 1 was found 25 µg/mL for both EMRSA-17 and clinical isolates. The MICs of the tested drugs were found to be much higher than compound 1, indicating that the organisms were actively using their resistance mechanism. MICs of amikacin, chloramphenicol, ciprofloxacin, clindamycin, erythromycin, gentamicin, neomycin, oxacillin, penicillin, streptomycin and sulfamethoxazole were found to be 2084, 1024, 1024, 1024, 1024, 512, 256, 4096, 2084, 2084 and 2084 µg/mL, respectively, for EMRSA-17. However, when they were dispensed in combination with compound 1, the MIC reduced to 2 to 16 pg/mL, respectively. This dramatic lowering of MIC (over 1000 fold) in combination of above mentioned drugs showed substantial synergistic action, while streptomycin showed partial synergistic effect.

Similarly the MICs of amikacin, chloramphenicol, ciprofloxacin, clindamycin, erythromycin. gentamicin, neomycin, oxacillin, penicillin, streptomycin and sulfamethoxazole and streptomycin in combination of compounds were also dramatically reduced to 5, 8, 8, 8, 8, 8, 8, 16, 8, 8, and 4 µg/mL respectively, against clinical isolates. This joint activity in all combination showed a strong element of synergism with above mentioned drugs, while clindamycin showed only a partial synergistic activity.

Discussion: Combinations of antibiotics and other compounds are commonly used in medicinal practices, such as augmenting (amoxicillin and clavulanate) to expand the spectrum of antimicrobials, and to produce the synergistic effects.

Fractional Inhibitory Concentration Index (FICI) is the sum of FICs of drugs +test compounds. In brief, the combination of test compound and drugs (antibiotics) exerts synergistic or additive effects on the growth of bacteria, as compared to single antimicrobial agent (Amber Farooqui et al., 2008).

By employing the phenomenon of combinational therapy studied by Sato and colleagues (2004), who observed that 6, 7-dihydroxyflavone had a weak antibacterial effect on MRSA, but at sub-MIC concentration it elevate the susceptibility to β-lactam antibiotics (Bakar et al. 2012).

In our study, we observed that most of the drugs (antibiotics)were inactive or poorly active at highest dosage against the MDR strains, but combination of drugs and compound 1 even at very lowest concentration dramatically increases the susceptibility of drugs. Therefore, most of the drugs that were required with an exceedingly high MICs value such as 1000 µg/mL or more to inhibit the MDR strains, were now reduced up to 4-8 µg/mL when experienced in combination with compound 1.

EXAMPLE 4

Increased Sensitivity of MDR Bacteria to Drugs through Inhibition of the MDR Efflux Pumps Assay Protocol: Protocol of Kalle et al, (2009) was employed with some modifications. Control cells were not exposed with any test compound or antibiotic. Combination of test compound and antibiotics were incubated for 3 hrs in test cells. Ethiduim bromide (EtBr) was added in to the Eppendorff, containing the combination of both drugs and compound. Cells with the drugs were also incubated and stained with EtBr. Control and treated samples were centrifuged for 3 min at 13,000 rpm. Supernatant was dissolved and the pallet was washed with PBS. Positive control contains ethidium bromide, while negative control was EtBr free. Flow cytometric analysis was carried out done by using the FL2 channel.

Flow cytometry data acquisition: The flow cytometric assay was performed. A total of 50,000 cells were counted by using Cell Quest software (BD) for data acquisition and analysis. EtBr was excited at 488 nm and the fluorescence detected through a 585 nm filter (FL-2 channel).

Results: The efflux pump studies were conducted on flow cytometer by using ethidium bromide dye which binds to or intercalates with DNA. Data was collected between the FL2 and cell counts which showed different histogram pattern of peaks of controls (labeled with EtBr, unlabeled), drugs (antibiotics) alone, and in combination of drugs with the compound 1 (FIGS. 2 and 3).

The fluorescent dye (EtBr) only stains the dead and dying or injured cells and excluded out from the living ones throud the active efflux system. The given overlays showed the unlabeled/labeled and drug (antibiotic) treated peaks revealed the normal bacterial size, confined in a starting region of the histogram, while bacteria treated with the compound 1 along with antibiotics were not able to effluxing out the EtBr, indicating that this combination alters or inhibit the efflux pump of organism.

Even with higher concentrations of antibiotics, all bacterial cells were found to be viable over the experimental period indicating the over expressed efflux system.

During the exposure of bacterial cells with compound 1, physical alteration in cell wall was also observed. Cellular granularities, as well as complexity, were affected/ changed as evident from the enhanced fluorescence intensities. In treated cells (antibiotics+compounds), prominent peaks shifting was observed in comparison to both the control cell population and drug alone. As a result, significant shift in the intensity of the red fluorescence of EtBr inside the cells was observed. Thus might be due to the presence of compound 1.

Discussion: With the combination of antibiotics and the compound 1, decrease in the efflux activity was observed, associated with a significant increase in the amount of cell-associated fluorescence. This indicated the capacity of compound 1 to inhibit the efflux pump of bacterial cells.

Combinational therapy by using the efflux pump inhibitors (test compounds) and antibiotics has been shown to increase the intracellular concentration of antibiotics, there by reversing, the resistance (Kalle and Rizvi et al., 2011).

In brief, compound 1 facilitates the accumulation of drug in the resistant strains as observed through EtBr efflux assay. This indicated the potential of compound 1 to significantly reverse the multidrug resistance and to increase the sensitivity of bacteria towards existing antibiotics, even at very low concentrations.

EXAMPLE 5

Compound Induced Damage through Production Reactive Oxygen Species ($O_2^-$) in MDR *Staphylococcus aureus* in Lucigenin CL Assay Assay Protocol: Protocol of Albesa et al (2002) was followed with slight modifications. $5 \times 10^5$ Cells were treated with the different concentrations of test compounds. Cells with compounds were incubated with leueigenin and filtered phosphate buffer saline. DMSO was added to the each well at the time of RLU determination to trigger the reaction. Negative control does not contain any test compound and DMSO. Positive control contains DMSO, but not the test compound. Determination by chemiluminescence (CL) was performed at room temperature by luminometer. The light emission results were measured in relative light unit (RLU).

Stimulation of ROS production in bacteria by antibiotics might be the main factor that contributes in the alteration of physiology of bacterial cells (Becerra et al., 2002).

Results: In Lucigening CL assay, more production of $O_2^-$ was observed after the treatment of cells EMRSA-17 and clinical isolates with compound 1 (FIG. 4). A comparison of positive and negative controls, the production and liberation of intracellular $O_2^-$ was not observed even in the presence of activator (DMSO). This clearly indicated that the damage occurred due to the production of intracellular $)_2^-$ induced by compound 1. Even very minute quantity of $O_2^-$, associated with the accumulation of compound 1, in the cells can cause cell damage.

Discussion: Many classes of antibiotics, regardless of their site of actions. promotes the generation of lethal hydroxyl radicals in both gram positive and gram negative bacteria (Dwyer et al., 2009). During this study, when MDR cells were treated with compound 1, $O_2^-$ were generated which damaged the cell effectively by direct attack. ROS ($O_2^-$) generation were also contributed in altering the physiology of the cells and cause cell death. A higher $O_2^-$ level was observed in compound 1 treated cells in a dose dependent manner, which indicated the bacterial cell damaged by the formation of ROS.

TABLE 1

High throughput screening assay (MABA) against MDR S. aureus.

| IUPAC Name | Structure | Source | % Inhibition 20 µg/mL EMRSA-17 | % Inhibition 20 µg/mL Clinical Isolates | % Inhibition 20 µg/mL EMRSA-16 | % Inhibition 20 µg/mL MRSA-252 |
|---|---|---|---|---|---|---|
| Artonin 1 (1) | 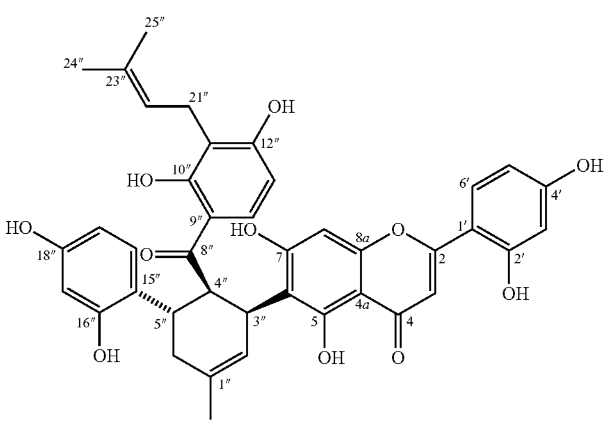 | *Morus mesozygia* Stapf. | 91.109 | 88.892 | 88.736 | 69.438 |

TABLE 2

Reversal of Multi-Drug Resistance in EMRSA-17 by Artonin I (1).

| Antibiotic | MIC (a)* µg/mL | MIC (b)* µg/mL | MIC (a + b)* µg/mL | FIC (a) µg/mL | FIC (b) µg/mL | FIC (s) µg/mL | Effect |
|---|---|---|---|---|---|---|---|
| Amikacin | 256 | 25 | 8 | 0.0312 | 0.320 | 0.3512 | Synergistic |
| Chloramphenicol | 1024 | 25 | 8 | 0.0078 | 0.320 | 0.3278 | Synergistic |
| Ciprofloxacin | 1024 | 25 | 4 | 0.0039 | 0.16 | 0.1639 | Synergistic |
| Clindamicin | 4096 | 25 | 8 | 0.0019 | 0.320 | 0.3219 | Synergistic |

TABLE 2-continued

Reversal of Multi-Drug Resistance in EMRSA-17 by Artonin I (1).

| Antibiotic | MIC (a)* µg/mL | MIC (b)* µg/mL | MIC (a + b)* µg/mL | FIC (a) µg/mL | FIC (b) µg/mL | FIC (s) µg/mL | Effect |
|---|---|---|---|---|---|---|---|
| Erythromycin | 2048 | 25 | 8 | 0.0038 | 0.320 | 0.3238 | Synergistic |
| Gentamicin | 1024 | 25 | 4 | 0.0039 | 0.16 | 0.1639 | Synergistic |
| Neomycin | 512 | 25 | 8 | 0.1562 | 0.320 | 0.3356 | Synergistic |
| Oxacillin | 2084 | 25 | 2 | 0.0009 | 0.08 | 0.0809 | Synergistic |
| Penicillin | 1024 | 25 | 4 | 0.0039 | 0.16 | 0.1639 | Synergistic |
| Streptomycin | 2048 | 25 | 16 | 0.0076 | 0.640 | 0.6470 | Partial Synergistic |
| Sulfamethoxazole | 2048 | 25 | 8 | 0.0038 | 0.320 | 0.3238 | Synergistic |

*Antibiotics (a) and *Compounds (b)
MIC (a), MIC (b): Minimal Inhibitory Concentration of Antibiotics and Compound 1
FIC (a), FIC (b): Fractional Inhibitory Concentration of Antibiotics and Compound 1
FIC (s): a + b = s

TABLE 3

Reversal of Multi-Drug Resistance in Clinical Isolates by Artonin I (1).

| Antibiotic (a) | MIC (a)* µg/mL | MIC (b)* µg/mL | MIC (a + b)* µg/mL | FIC (a) µg/mL | FIC (b) µg/mL | FIC (s) µg/mL | Effect |
|---|---|---|---|---|---|---|---|
| Amikacin | 128 | 25 | 8 | 0.0625 | 0.320 | 0.3825 | Partial Synergistic |
| Chloramphenicol | 1024 | 25 | 8 | 0.0078 | 0.320 | 0.3278 | Synergistic |
| Ciprofloxacin | 1024 | 25 | 8 | 0.0078 | 0.320 | 0.3278 | Synergistic |
| Clindamicin | 4096 | 25 | 16 | 0.0039 | 0.64 | 0.6446 | Synergistic |
| Erythromycin | 2048 | 25 | 8 | 0.0038 | 0.320 | 0.3238 | Synergistic |
| Gentamicin | 512 | 25 | 8 | 0.0156 | 0.320 | 0.3356 | Synergistic |
| Neomycin | 1024 | 25 | 8 | 0.0078 | 0.320 | 0.3278 | Synergistic |
| Oxacillin | 2084 | 25 | 5 | 0.0023 | 0.200 | 0.2023 | Synergistic |
| Penicillin | 2084 | 25 | 8 | 0.0038 | 0.320 | 0.3238 | Synergistic |
| Streptomycin | 2048 | 25 | 4 | 0.0019 | 0.160 | 0.1619 | Synergistic |
| Sulfamethoxazole | 2048 | 25 | 8 | 0.0038 | 0.320 | 0.3239 | Synergistic |

*Antibiotics (a) and *Compounds (b)
MIC (a), MIC (b): Minimal Inhibitory Concentration of Antibiotics and Compound 1
FIC (a), FIC (b): Fractional Inhibitory Concentration of Antibiotics and Compound 1
FIC (s): a + b = s

What is claimed is:

1. A method of treating infections resulting from resistant strains of *Staphlococcus aureus* comprising administering to a patient in need of such treatment an effective amount of a flavonoid Artonin I

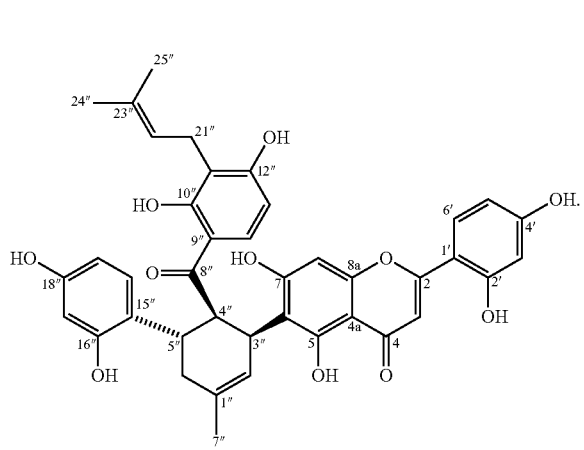 [SMILES: CC(C)=CCc1c(O)ccc(C(=O)[C@H]2[C@@H](c3c(O)cc4oc(-c5ccc(O)cc5O)cc(=O)c4c3O)C=C(C)C[C@@H]2c2ccc(O)cc2O)c1O]

2. A method of treating an infection resulting from resistant strains of *Staphlococcus aureus* comprising administering to a patient in need of such treatment an effective amount of a flavonoid Artonin I

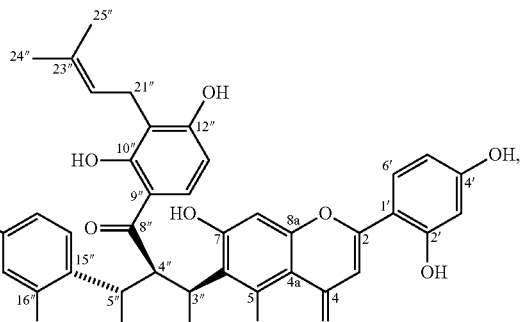

and an antibiotic selected from the group consisting of amikacin, chloramphenicol, ciprofloxacin, clindamycin, erythromycin, gentamicin, neomycin, oxacillin, penicillin, streptomycin and sulfamethoxazole.

* * * * *